(12) United States Patent
Hughett et al.

(10) Patent No.: US 6,659,934 B1
(45) Date of Patent: Dec. 9, 2003

(54) AUTOMATED SYSTEM FOR THE RADIATION TREATMENT OF A DESIRED AREA WITHIN THE BODY OF A PATIENT

(75) Inventors: James D. Hughett, Lawrenceville, GA (US); Robert Michael Webster, Duluth, GA (US); Douglas Layland Armstrong, Atlanta, GA (US); Byron Lee Boylston, Woodstock, GA (US); Gregg T. Juett, Clearwater, FL (US); Richard A. Hillstead, Duluth, GA (US); Jack C. Griffis, III, Decatur, GA (US); Andrew L. Lerohl, Hoschton, GA (US); Mark Dehdashtian, Costa Mesa, CA (US); Marvin A. Guiles, Stow, MA (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 09/469,510

(22) Filed: Dec. 22, 1999

Related U.S. Application Data

(60) Provisional application No. 60/113,406, filed on Dec. 22, 1998.

(51) Int. Cl.[7] .................................................. A61N 5/00
(52) U.S. Cl. ................................... 600/7; 600/3; 600/4
(58) Field of Search ............................... 604/151, 131; 417/478, 217, 238; 600/3–8, 1, 2

(56) References Cited

U.S. PATENT DOCUMENTS 2,750,517 A    6/1956   Baum
2,965,761 A   12/1960   Horvath (List continued on next page.)

FOREIGN PATENT DOCUMENTS

| CA | 1197631 | 12/1985 |
| DE | 1095963 | 12/1960 |
| GB | 1219604 | 1/1971 |
| GB | 1558127 | 12/1979 |
| SU | 279814  | 7/1975 |

OTHER PUBLICATIONS

International Search Report (International Application No. PCT/US99/30000), dated May 31, 2000.

English abstract re German patent application No. DE 1095963, published Dec. 29, 1960.

Primary Examiner—Brian L. Casler
Assistant Examiner—Kevin C. Simmons
(74) Attorney, Agent, or Firm—Cook, Alex, McFarron, Manzo, Cummings & Mehler, Ltd.

(57) ABSTRACT

A transfer device usable in a system for intraluminal treatment of a selected site in a body of a patient in which the transfer device comprises an integral pump for pressurizing and circulating fluid through a fluid path defined by the transfer device and associated catheter. A removable fluid cartridge is provided including a reservoir from which fluid is drawn by the pump and into which fluid is returned after being circulated through the fluid path. The pump may be a peristaltic pump and the fluid cartridge may include an elongated fluid pick-up having an inlet through which fluid is introduced into the transfer device. The fluid pick-up is sized in length so that the inlet is always submerged in the fluid regardless of the orientation of the transfer device.

9 Claims, 15 Drawing Sheets

U.S. PATENT DOCUMENTS

| | | |
|---|---|---|
| 3,088,032 A | 4/1963 | Brunton |
| 3,532,888 A | 10/1970 | Masefield et al. |
| 4,233,517 A | 11/1980 | van't Hooft |
| 4,584,991 A | 4/1986 | Tokita et al. |
| 4,733,653 A | 3/1988 | Leung et al. |
| 4,745,907 A | 5/1988 | Russel, Jr. et al. |
| 5,030,194 A | 7/1991 | van't Hooft |
| 5,032,113 A | 7/1991 | Burns |
| 5,103,395 A | 4/1992 | Spako et al. |
| 5,147,282 A | 9/1992 | Kan |
| 5,533,969 A | 7/1996 | Mulder |
| 5,683,345 A | 11/1997 | Waksman et al. |
| 5,776,091 A * | 7/1998 | Brugger et al. ............... 604/29 |
| 5,800,383 A * | 9/1998 | Chandler et al. ............. 604/35 |
| 5,851,172 A | 12/1998 | Bueche |
| 5,899,882 A | 5/1999 | Waksman et al. |
| 6,013,020 A | 1/2000 | Meloul et al. ................. 600/7 |
| 6,048,300 A | 4/2000 | Thornton et al. |
| 6,077,055 A * | 6/2000 | Vilks ........................ 417/44.2 |
| 6,358,237 B1 * | 3/2002 | Paukovits et al. .......... 604/151 |

* cited by examiner

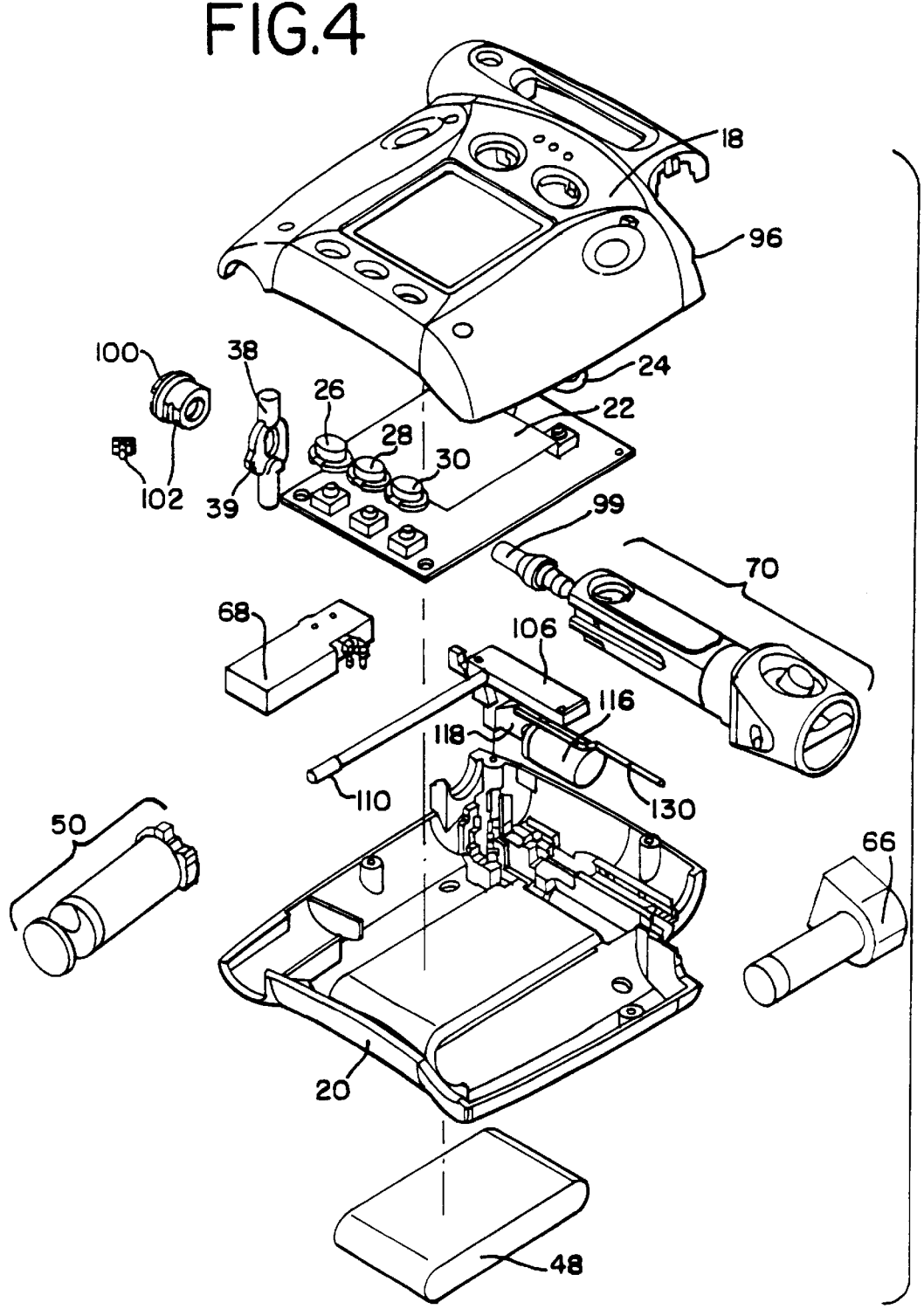

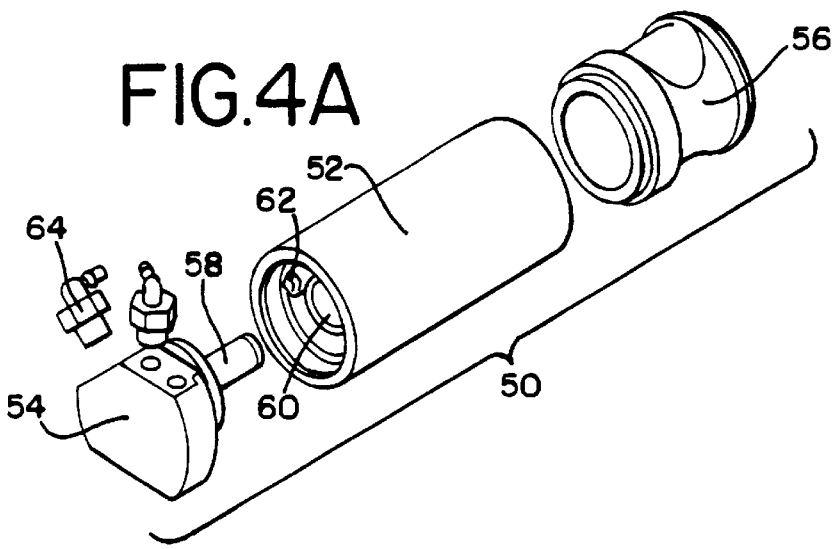
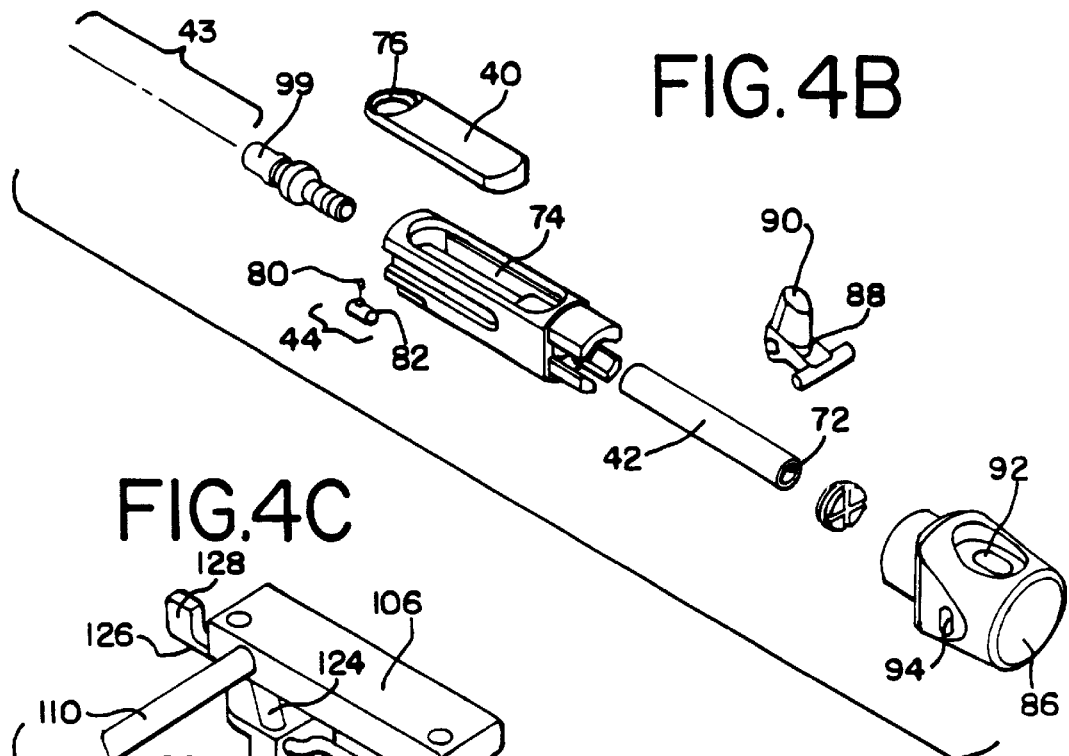
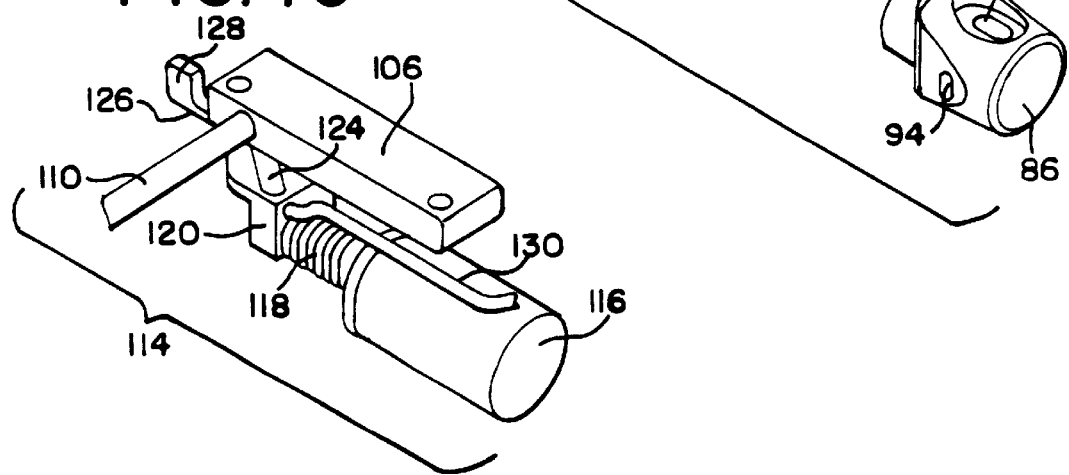

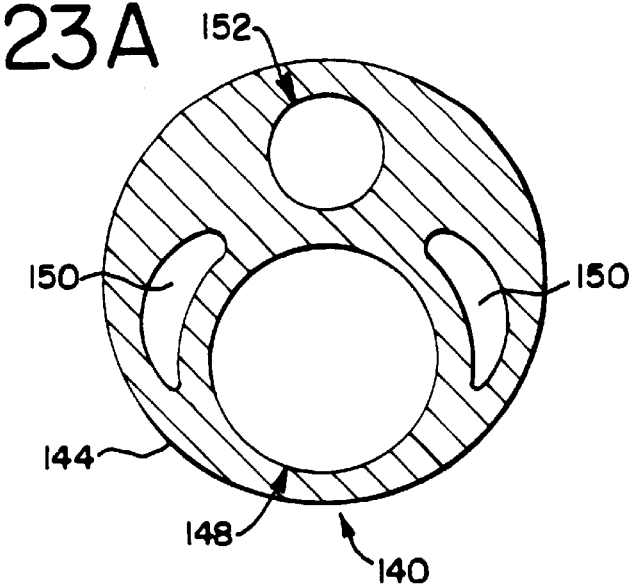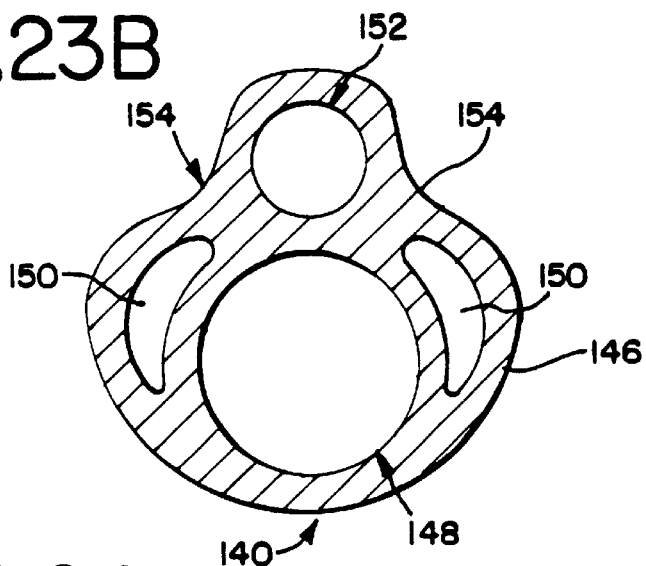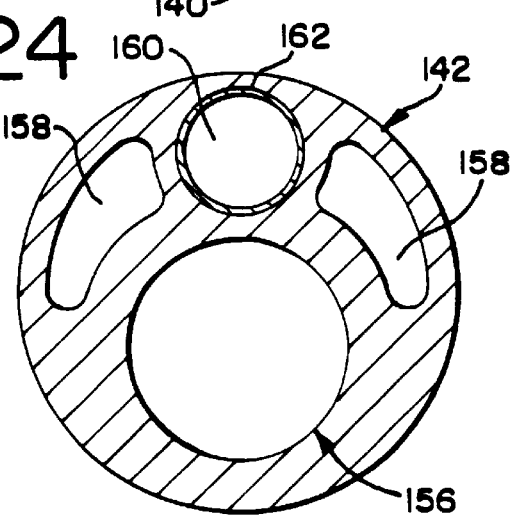

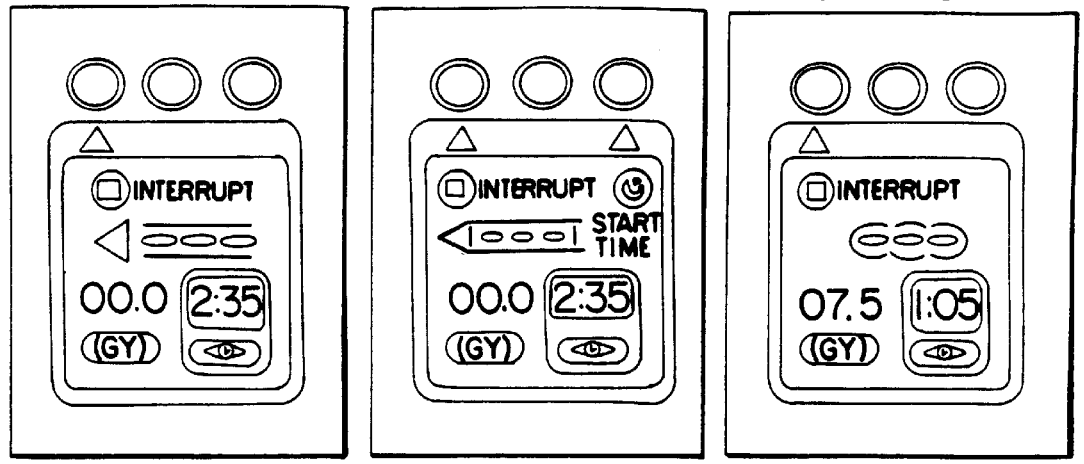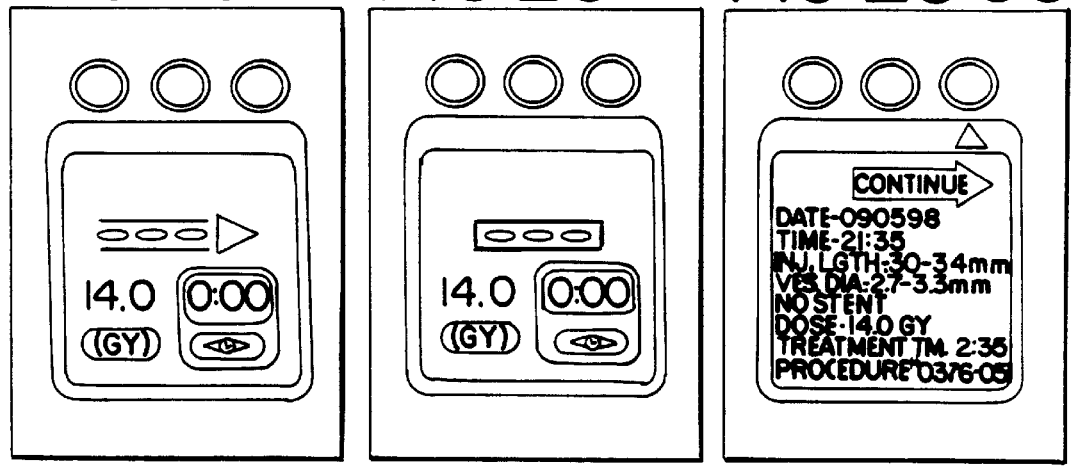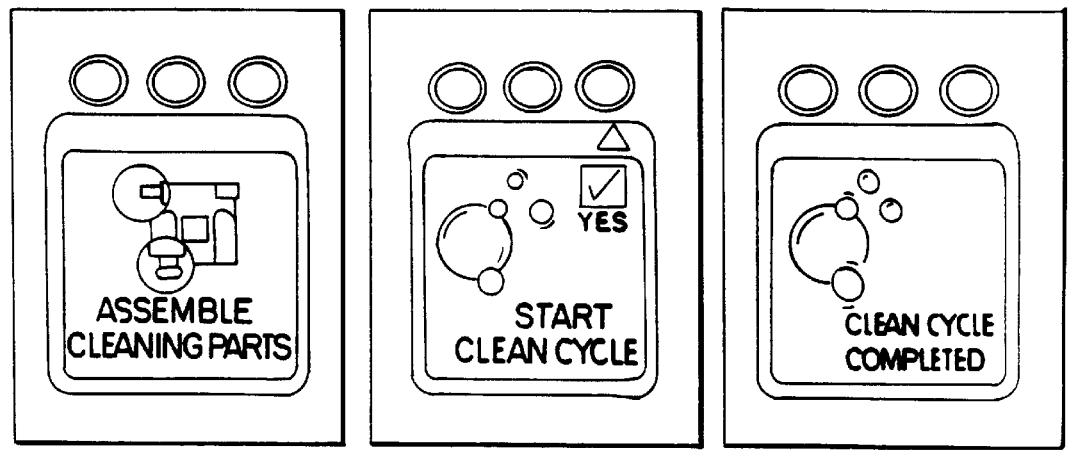

AUTOMATED SYSTEM FOR THE RADIATION TREATMENT OF A DESIRED AREA WITHIN THE BODY OF A PATIENT

CROSS-REFERENCE TO RELATED APPLICATION

This application claims the benefit of U.S. Provisional Application Ser. No. 60/113,406 filed Dec. 22, 1998.

BACKGROUND OF THE INVENTION

The present invention relates generally to an intraluminal radiation system for the delivery of treatment elements by way of a catheter to a selected location within the intraluminal passageways of a patient. More particularly, the present invention relates primarily to an improved transfer device for handling the treatment elements and delivering them to the catheter and an improved catheter assembly.

Since the late1970's balloon angioplasty techniques have become widely used for opening blockages in coronary arteries. Briefly, the enlargement of the artery is achieved by advancing a balloon catheter into a narrowed portion of the artery and inflating the balloon to expand the diameter of the artery, thus opening the artery for greater blood flow. Atherectomy techniques, in which blockages are removed or reduced in size, have also been used to the same end.

While balloon angioplasty has proved an effective way of opening the coronary arteries, in a significant number of cases the arteries will narrow again at the location where the balloon was expanded, such narrowing being termed restenosis. Restenosis is believed to be caused by formation of scar tissue at the site of the angioplasty that results from the injury to the artery caused by the inflation of the balloon. More recently, intraluminal radiation has been used after angioplasty or atherectomy to treat the affected area of the artery to inhibit cell proliferation and wound healing response and, consequently, help to prevent restenosis. Methods and apparatus for such intraluminal radiation treatment are disclosed in U.S. Pat. Nos. 5,899,882, and 6,031,020, filed Sep. 23, 1997, and U.S. Pat. No. 6,261,219, filed May 4, 1999, all of which are incorporated herein by reference. These applications generally disclose an apparatus comprising a catheter, which is inserted intraluminally into the patient and advanced to the site of the area to be treated, and a transfer device for facilitating either the hydraulic or pneumatic advancement and retrieval of individual radioactive treating elements or "seeds" along the catheter to and from the treatment site.

As with any device inserted into the vascular system, it must have sufficient integrity to insure that no pieces or elements are separated from or exit the device into the vascular system. This is particularly true for the treating elements which are moved to and from the distal end of the catheter. Additionally, because the device is intended to use radioactive treating elements, there is a heightened need for safety to prevent any unintended exposure of either the patient or the user to radioactivity.

Actual use of the apparatus described in the above-identified patent and co-pending applications has suggested several areas where the device could be improved to reduce the possibility of having treatment elements escape from the system, thus enhancing patient and user safety.

Consequently, it is the principal object of the present invention to provide a transfer device and catheter assembly that has additional safeguards to protect the patient and user for unintended exposure to radiation.

More particularly, it is an object of the present invention to provide a transfer device/catheter assembly in which the treatment elements cannot be inadvertently released from the transfer device.

SUMMARY OF THE INVENTION

These objects, as well as others which will become apparent upon reference to the following drawings and detailed description, are provided by a transfer device usable in a system for intraluminal treatment of a selected site in a body of a patient in which the transfer device comprises an integral pump for pressurizing and circulating fluid through a fluid path defined by the transfer device and associated catheter. A removable fluid cartridge is provided including a reservoir from which fluid is drawn by the pump and into which fluid is returned after being circulated through the fluid path. The pump may be a peristaltic pump and the fluid cartridge may include an elongated fluid pickup having an inlet through which fluid is introduced into the transfer device. The fluid pick-up is sized in length so that the inlet is always submerged in the fluid regardless of the orientation of the transfer device. A removable treatment cartridge having a lumen forming part of the fluid path may also be provided, and a storage sleeve for the treatment cartridge may be of a radiation-blocking material, such as quartz. Further, the treatment cartridge may have a memory for storing and indicating selected information about the treating element.

In another aspect of the invention, the transfer device may include a system for preventing operation of the transfer device unless each of the catheter, fluid cartridge and treating or source cartridge are attached to the transfer device. In a preferred embodiment, such a system may comprise an illumination source and an optical sensor located in the transfer device in proximity to where each of the catheter, fluid cartridge, and source cartridge is received by the transfer device. Each illumination source is located with respect to its optical sensor so that the optical sensor is able to receive light from its illumination source only if the catheter, fluid cartridge or source cartridge is not received by the transfer device. The optical sensor is blocked from receiving light from the illumination source when the catheter, fluid cartridge or source cartridge are received by the transfer device. A microprocessor that controls movement of the treating element from the transfer device to the catheter prevents operation of the transfer device upon receiving a signal from any of the optical sensors indicating that at least one of the catheter, fluid cartridge, and source cartridge is not attached to the transfer device.

In a still further aspect of the invention, a catheter is provided for use in the intraluminal treatment system which has four lumens extending substantially along the length of the catheter, one lumen being sized to slidingly receive a treating element and being in fluid communication with two lumens at the distal end thereof for the return of fluid. The fourth lumen is open at the distal end to receive a guidewire. The catheter may have a distal end with a cross-sectional area smaller than the proximal end of the catheter, the cross-sectional shape being non-circular so as to permit perfusion.

In a further aspect of the invention, the transfer device includes a gate movable between first and second positions for selectively permitting or preventing the treating element from moving from the treating element cartridge to the catheter, with an actuator controlling the gate that also permits release of the catheter and the treating element cartridge from the transfer device only when the gate is in position to prevent the treating element from moving from the treating element cartridge to the catheter.

In a further aspect of the invention, the transfer device includes a system for detecting the presence or absence of the treating element in the storage sleeve including a light source disposed on one side of the storage sleeve and a linear array of photosensors disposed on a second side of the storage sleeve. A microprocessor is provided for comparing the amount of light measured by the photosensors to a reference amount corresponding to the amount of light measured by the photosensors when the treating element is not within the lumen of the storage sleeve.

DRAWINGS

FIG. 4 is an exploded view of the automated transfer device of FIG. 1 including a fluid cartridge, a source cartridge, and a gate actuator assembly.

FIG. 4A is an exploded view of the fluid cartridge of FIG. 4.

FIG. 4B is an exploded view of the source cartridge of FIG. 4.

FIG. 4C is an enlarged view of the gate actuator assembly of FIG. 4.

FIG. 23A is a cross-sectional view of the proximal end of a delivery catheter in accordance with the present invention.

FIG. 23B is a cross-sectional view of the distal end of the catheter of FIG. 23A.

FIG. 24 is a cross-section view of a delivery catheter of the present invention.

Figure 1:
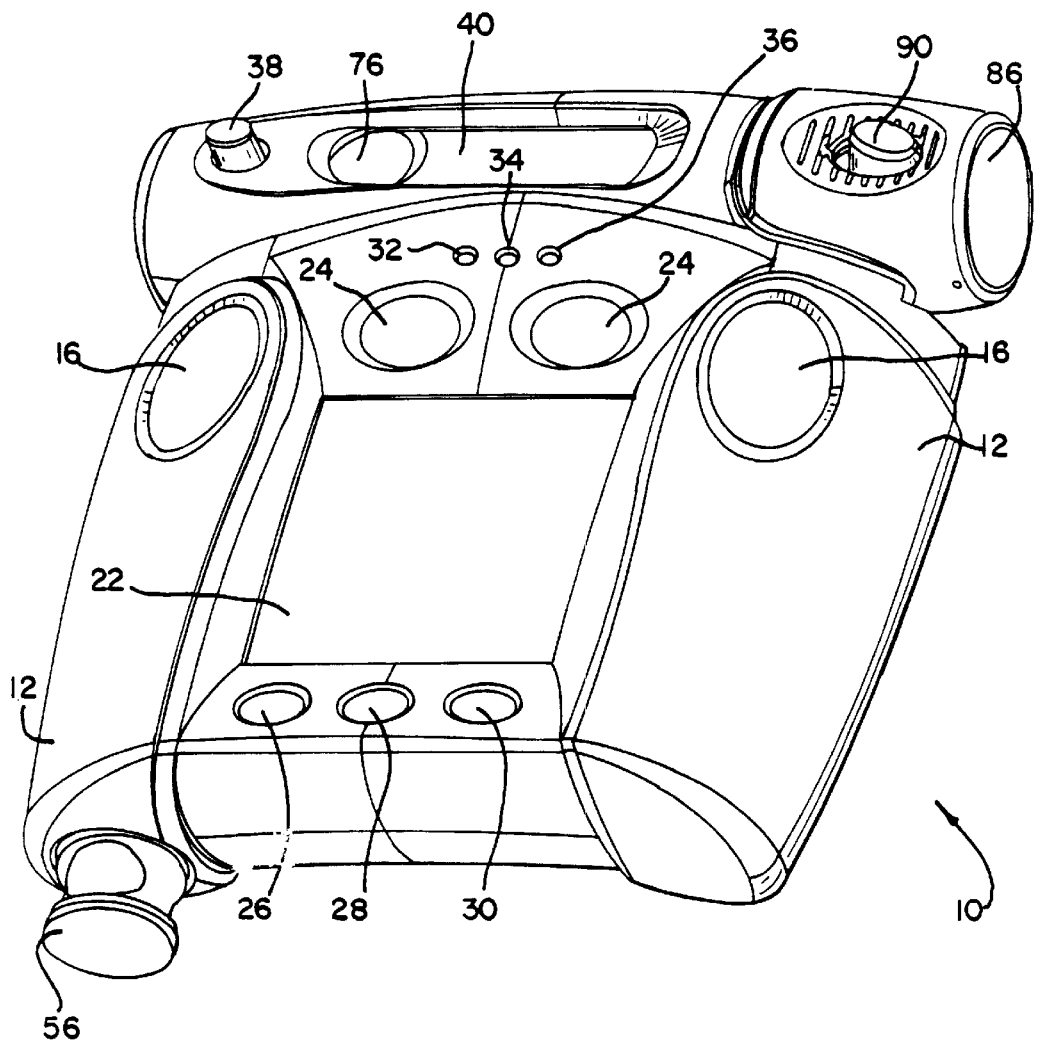
FIG. 1 is a perspective view of an automated transfer device in accordance with the present invention.
Figure 25A:
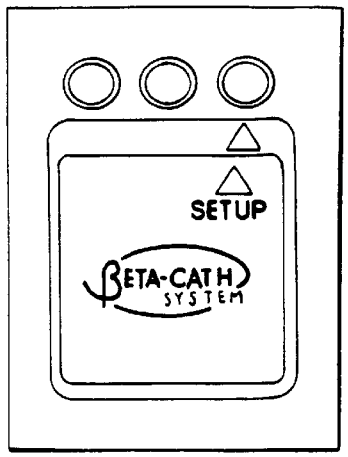
Figure 25B:
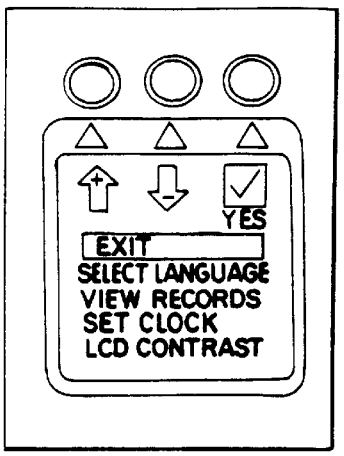
Figure 25C:
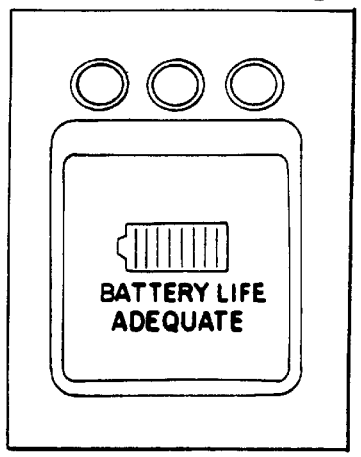
Figure 25D:
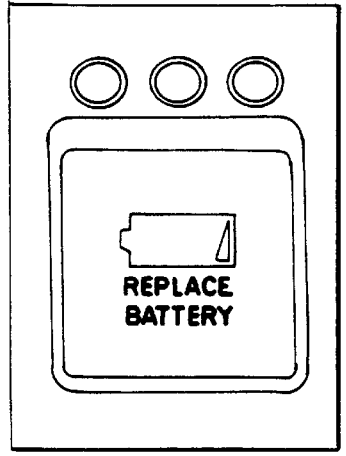
Figure 25E:
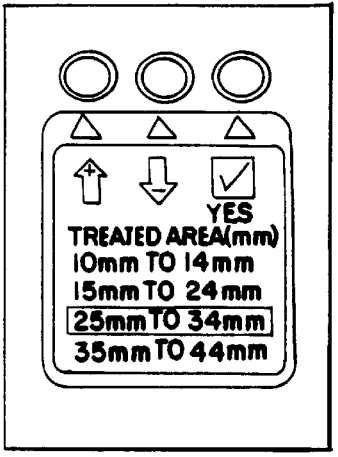
Figure 25F:
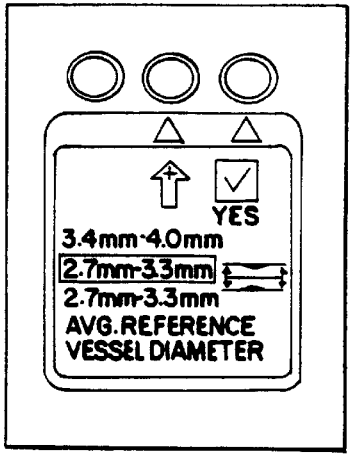
Figure 25G:
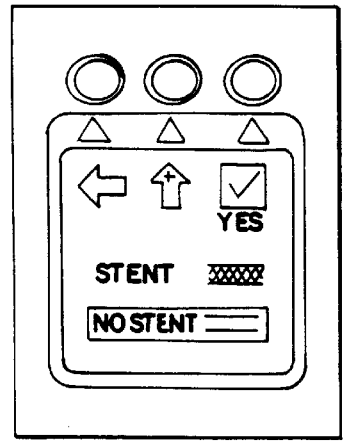
Figure 25H:
Figure 25I:
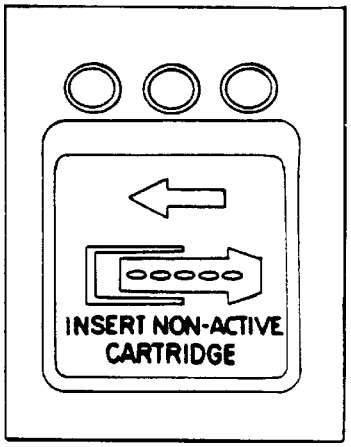
Figure 25J:
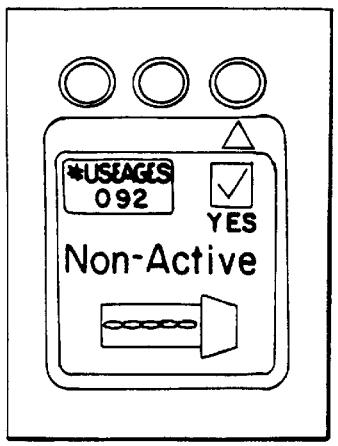
Figure 25K:
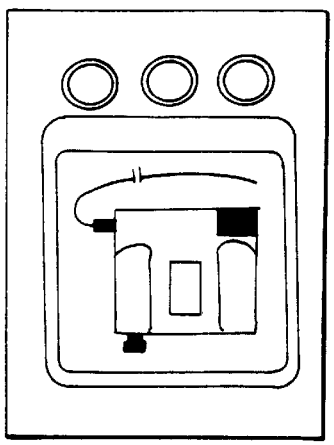
Figure 25L:
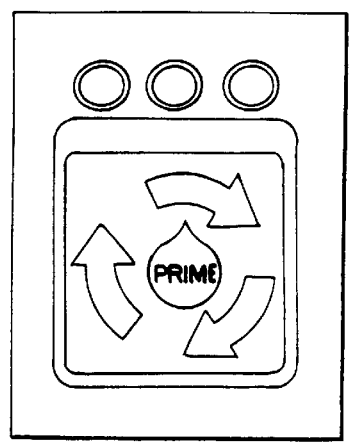
Figure 25M:
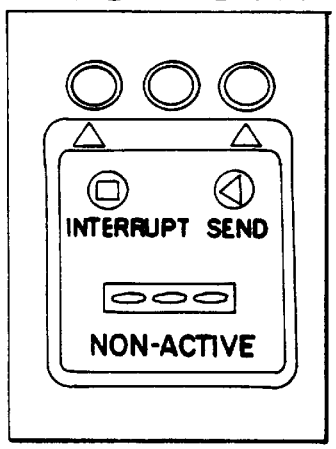
Figure 25N:
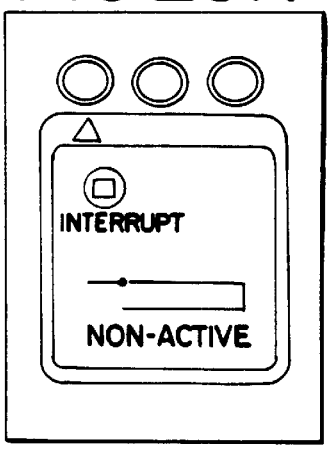
Figure 25O:
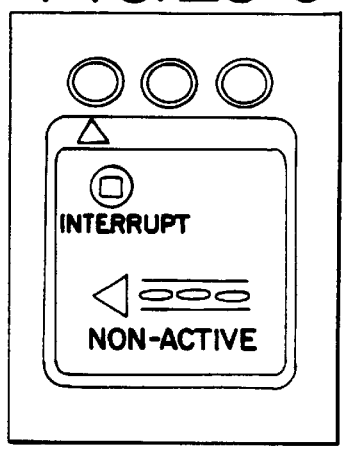
Figure 25P:
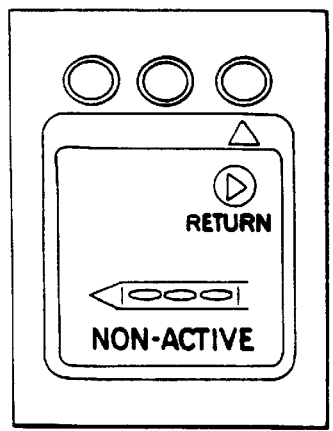
Figure 25Q:
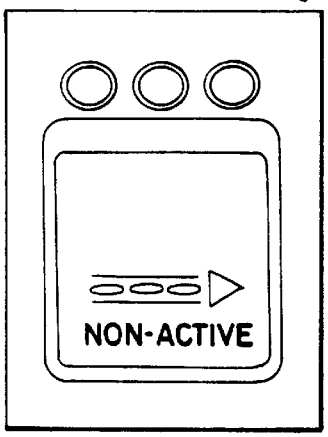
Figure 25R:
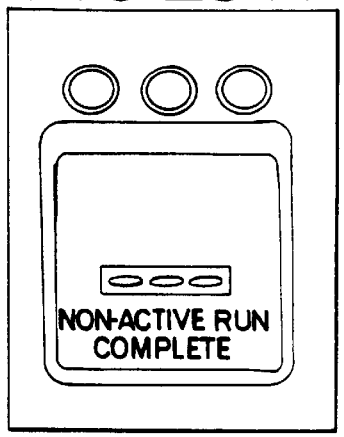
Figure 25S:
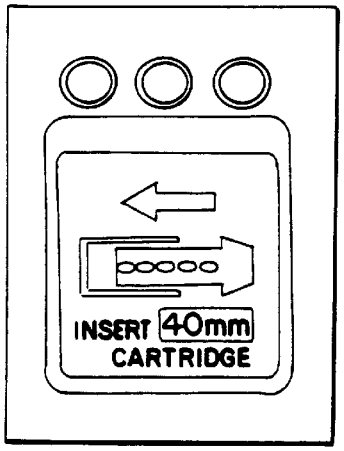
Figure 25T:
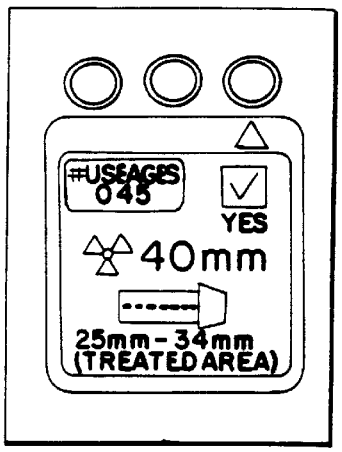
Figure 25U:
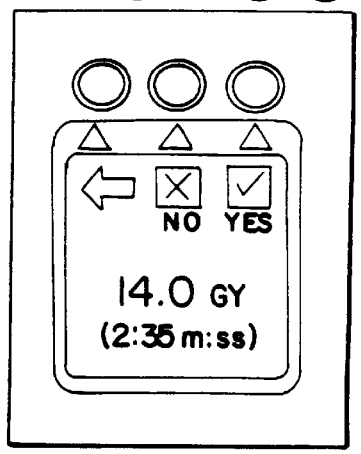
Figure 25V:
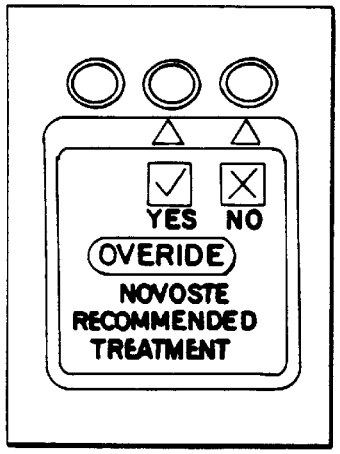
Figure 25W:
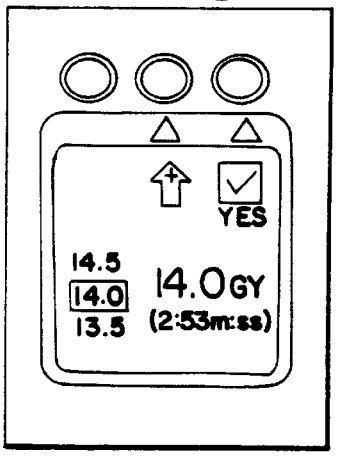
Figure 25X:
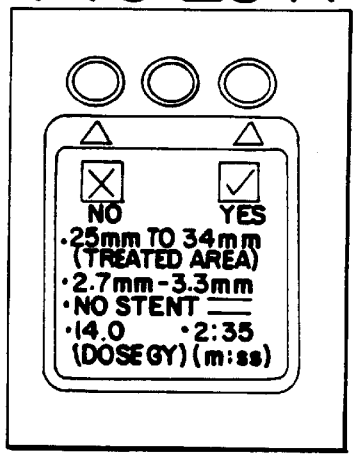
Figure 25Y:
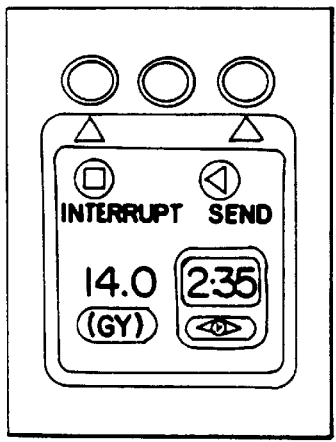
Figure 25Z:
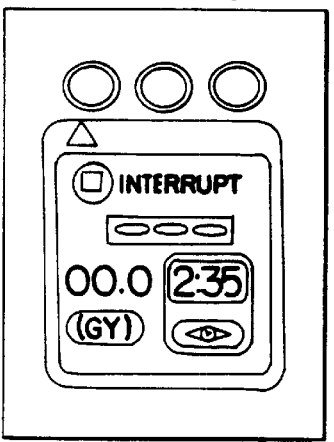
Figure 25A:
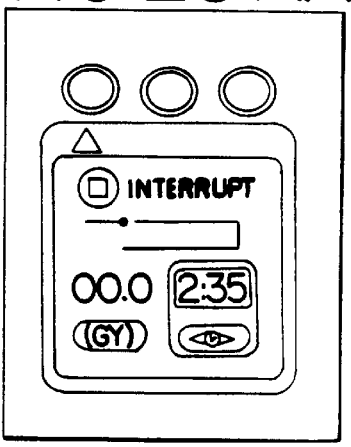
Figure 25:
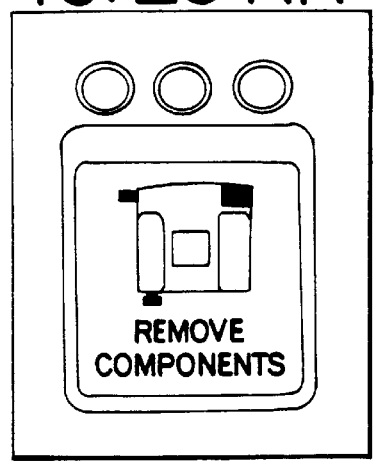
Figure 25:
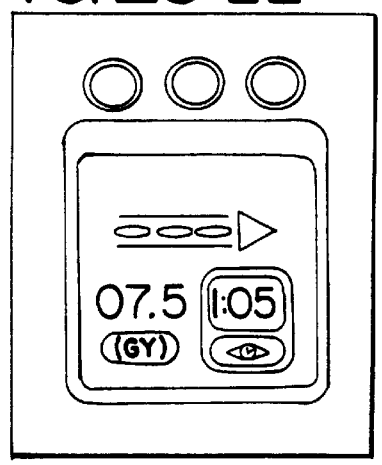
Figure 25:
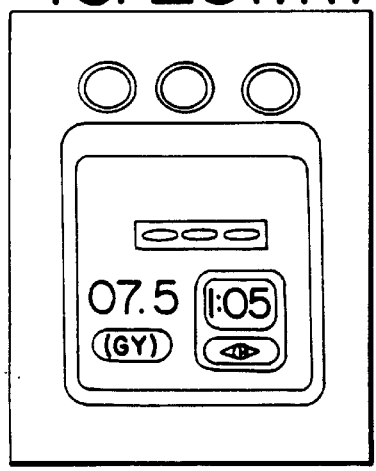
Figure 25:
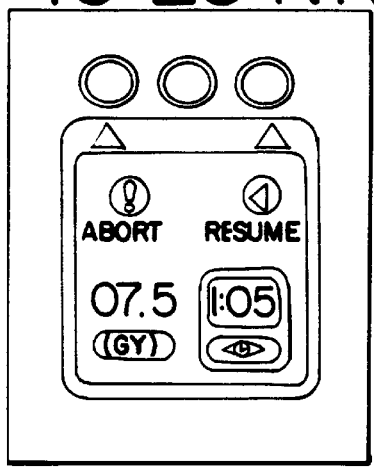
Figure 25:
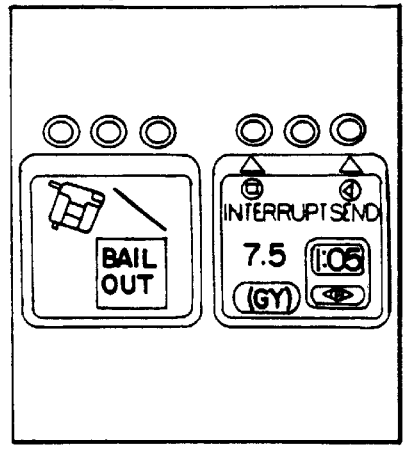
Figure 25:
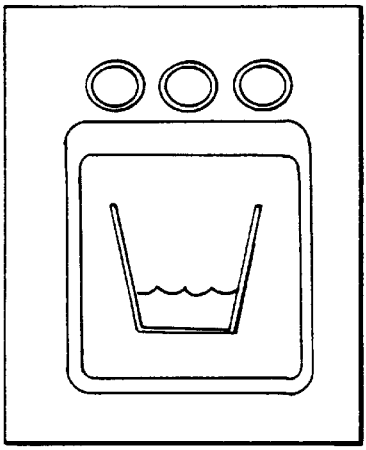

FIGS. 25 A–PP are graphical representations of an alternative series of display screens that are displayed by the automated transfer device of FIG. 1.

DETAILED DESCRIPTION

The present invention comprises an automated catheter based radiation delivery system and its method of use for treatment of a desired area within the body of a patient. The system includes a delivery catheter, treatment elements, and a transfer device that electromechanically delivers the source train through the catheter to the selected location within a patient's body. The transfer device prompts the user to proceed appropriately through the procedure by displaying graphics and text via a LCD (Liquid Crystal Display) with a series of individual display prompts combining with operative input controls allows for an intuitive user interface.

Figure 3:
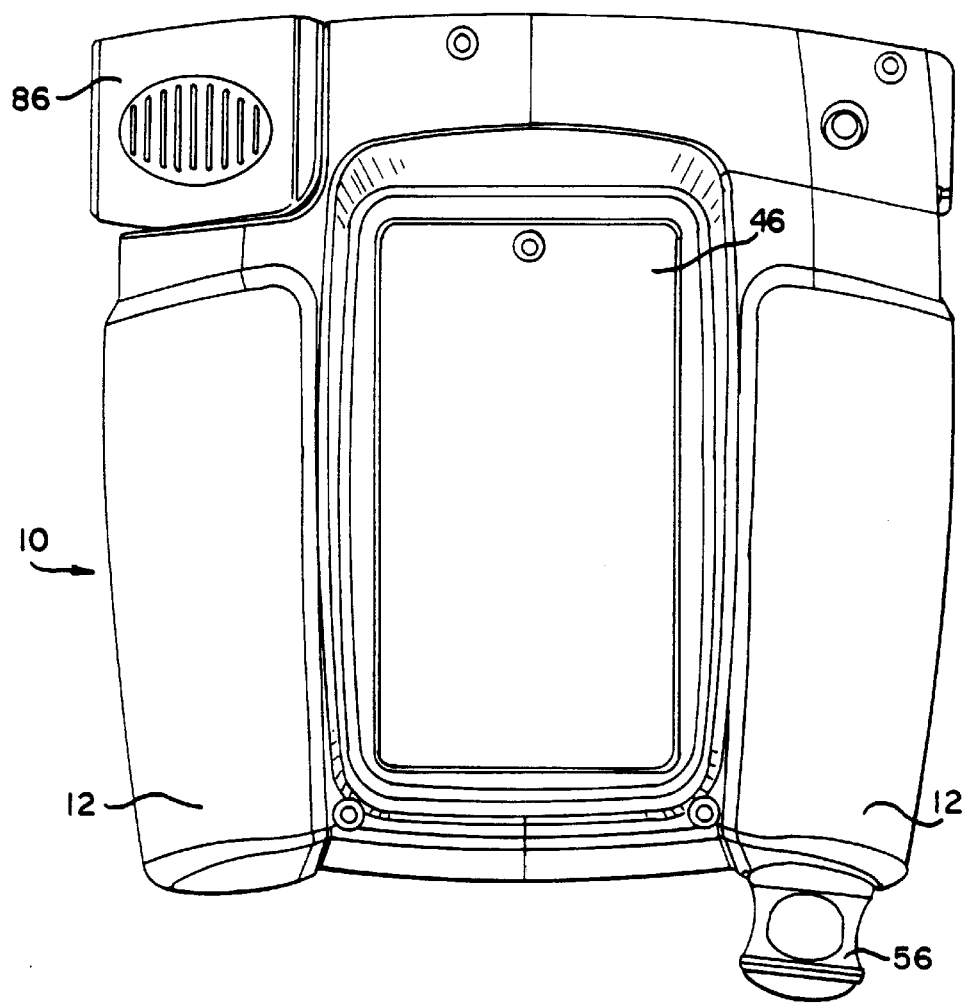
FIG. 3 is a bottom view of the automated transfer device of FIG. 1.
Figure 2:
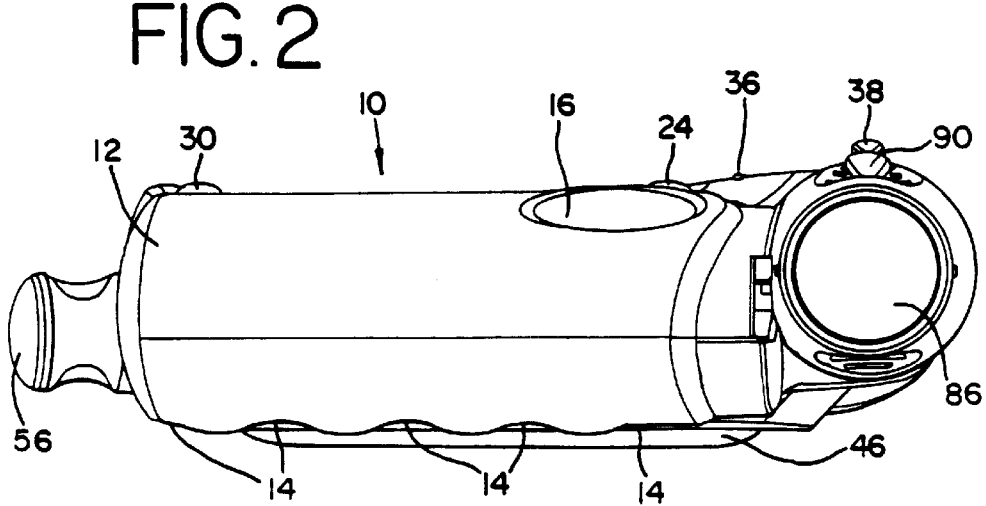
FIG. 2 is a side view of the automated transfer device of FIG. 1.

The assembled transfer device can be seen in FIGS. 1–3. The exterior of the transfer device 10 is ergonomically designed to be easily held with either or both hands, making it equally adaptable for right and left-handed clinicians. As can be seen in FIGS. 1 and 2, curved handgrips 12 with finger rests 14 and thumb rests 16 are located on both the left and right sides of the transfer device 10. Alternatively, the device 10 can rest in the palm of the user's hand or on a flat surface. The controls are easily reachable with the thumbs when both hands are supporting the device.

An upper housing portion 18 and a lower housing portion 20 fit together to create the shell that holds the internal components. Openings in the upper housing portion 18 allow a user to access a display 22, control buttons 24, 26, 28, 30, indicator LEDs (Light-emitting Diodes) 32, 34, 36, and a latch member 38. The upper portion 18 also includes a window 40 for viewing a sleeve 42, which houses a source train 43 (comprising treatment elements and marker seeds), and a pin gate 44. The sleeve 42 is preferably made of a radiation-blocking material, such as quartz, synthetic fused silica, polycarbonate plastic, etc.

The lower housing portion 20 has a central opening for mounting the power supply for the device, most likely a replaceable or rechargeable battery pack 48. A hard cover 46, as shown in FIG. 2, is securely positioned over the power supply, completely closing the opening. The battery pack 48 may have an integrated plastic housing with external contacts that connect electrically with those on the transfer device 10 to ensure its ease of replacement or recharging. This battery pack would reside along the exterior of the transfer device 10 and be instantly accessible by the user.

The upper and lower housing portions 18, 20 together also create an opening for the insertion of a fluid cartridge assembly 50. The fluid cartridge 50 contains saline, sterile or distilled water, or some other fluid source for the hydraulic delivery of the source train 43.

Figure 5:
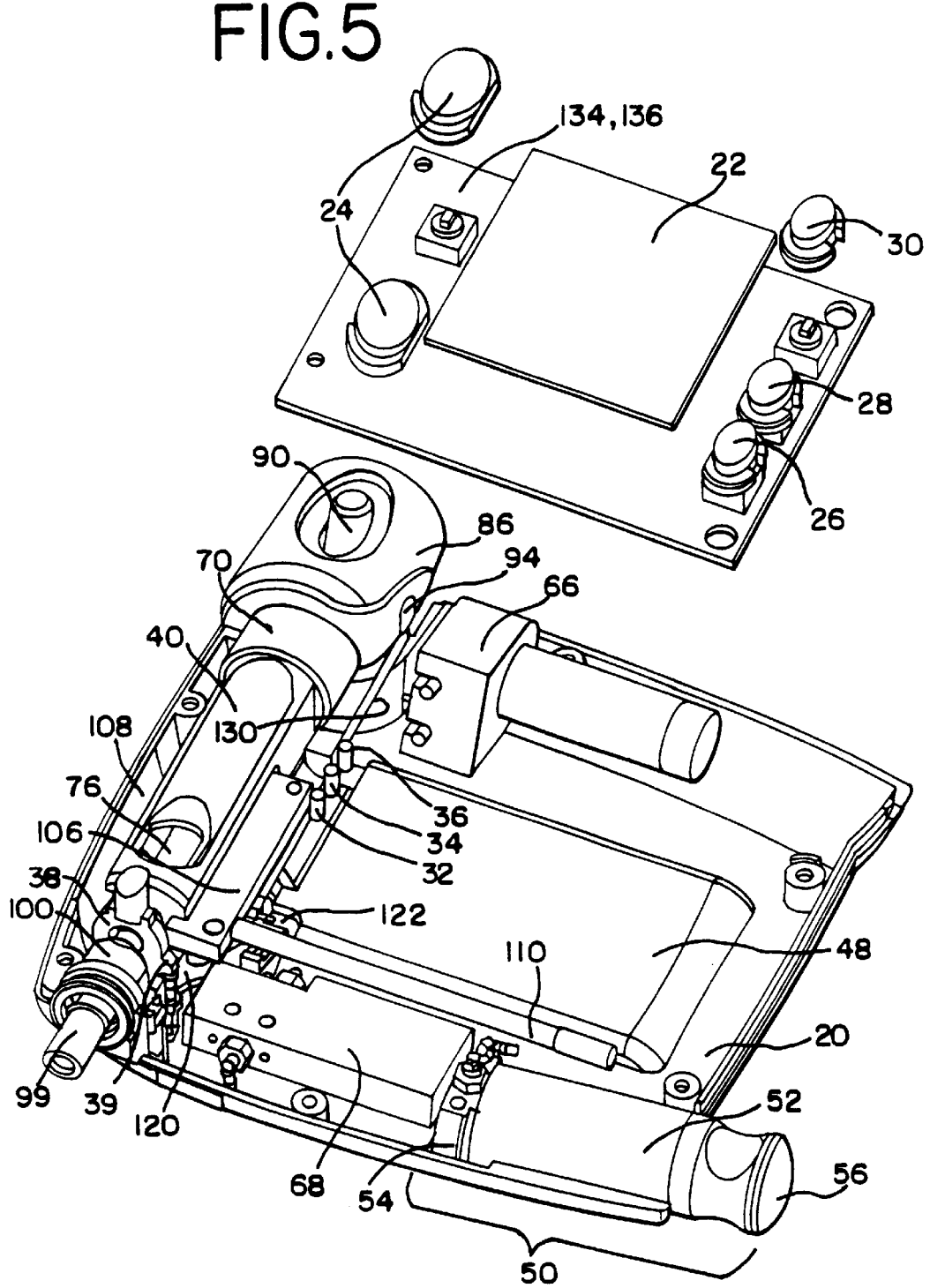
FIG. 5 is a perspective view of the automated transfer device of FIG. 1 with the upper half of the housing removed, with selected internal components shown in exploded view.

The fluid cartridge assembly 50 includes a cylindrical fluid reservoir 52, an end cap 54 that channels the fluid in and out of the fluid reservoir 52, and a handle 56 for insertion and removal of the fluid reservoir 52 with respect to the transfer device 10, best seen in FIGS. 4A and 5. The end cap 54 acts as a fluid manifold and comprises a fluid pick-up in the form of an elongated appendage 58 having a fluid channel or inlet through which fluid is introduced into the transfer device. The end cap 54 may be an integral part of the transfer device and adapted to mate with the fluid reservoir 52 upon its insertion into the transfer device. The distal center portion of the fluid reservoir 52 has a recessed opening 60 for the receipt of the fluid pick-up 58. Adjacent to the opening 60 is a fluid return hole 62 that allows fluid to return to the reservoir 52 after it has circulated through the transfer device and its associated catheter.

The dimensions of the reservoir 52 and the volume of the fluid ate such that the fluid level never falls below the recess 60 when handling the transfer device 10. The angle at which one holds the transfer device 10 may shift some fluid from one side of the recess 60 to the other, but the free end of the appendage 58 will always be submerged in fluid. Thus, only fluid can enter the fluid channels of the appendage 58. This is important because of the need to reduce the likelihood of air bubbles getting into the fluid path.

The fluid reservoir 52 is removable for cleaning and for replacing the used fluid with fresh fluid. It simply unscrews from the fixed end cap 54. Alternatively, the fluid cartridge 50 may be disposable. At the end of each treatment, the used fluid cartridge 50 can be discarded and replaced with a new pre-filled cartridge.

Figure 7:
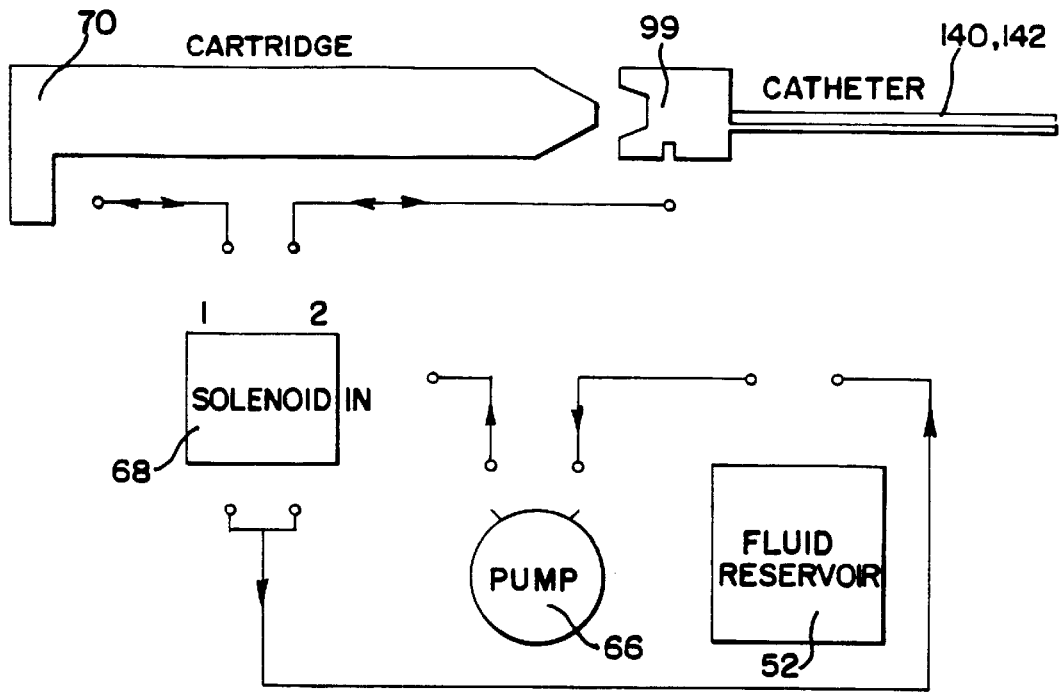
FIG. 7 is a schematic diagram showing the fluid flow path within the automated transfer device of FIG. 4.

As shown in the fluid flow diagram of FIG. 7, the fluid flow path begins within the fluid reservoir 52 and continues throughout the delivery system. The fluid cartridge exit port 64 (FIG. 4A) is in fluid communication with a peristaltic pump 66, which draws the fluid in and forces it through fluid channels to effectively deliver, maintain, and retrieve the treatment elements. The peristaltic pump 66 can be programmed to operate in a single direction for both sending and retrieving the treatment elements, or can be programmed to alternate directions between the sending and retrieving modes.

When pumping fluid in a single direction, the system relies on a fluid control valve, preferably a solenoid valve 68, working with the microprocessor to properly direct the fluid flow. Alternatively, a manual valve could be used to control the fluid flow. The fluid control valve 68 is in fluid communication with all fluid channels in both the source cartridge 70 and the attached delivery catheter 140 or 142. In the send mode, the fluid control valve 68 automatically directs the fluid flow through the source cartridge 70, into the catheter through the source delivery lumen, and out of the catheter through the fluid return channel. In the return mode, the fluid control valve 68 automatically reverses the direction of flow.

In use, greater force is required to send and retrieve the treatment elements to and from the catheter than to maintain them at a desired location in the catheter for treatment. Therefore, to conserve energy, the pump 66 operates at a decreased speed when maintaining the position of the treatment elements. When the treatment is complete, the pump 66 resumes full speed to force the treatment elements back into the source cartridge 70 within the transfer device 10. The pump 66 is idle when no treatment elements are being sent, maintained, or retrieved.

In the event the pump 66 becomes inoperable at a time when the treatment elements are not housed within the source cartridge 70, the user may manually override the automatic fluid management system to retrieve the elements. For example, a luer connector (not shown) accessible to the user may be in fluid communication with the fluid flow path, and a fluid filled syringe can be attached to the connector and used as a source of pressurized fluid to force the return of all treatment elements to the source cartridge 70.

In keeping with a further aspect of the invention, the transfer device 10 comprises an interchangeable source cartridge assembly 70 (best seen in FIG. 4). In order to be capable of delivering variable source train lengths, the source cartridge assembly 70 houses the quartz sleeve 42 which in turn houses the source train 43 and the pin gate 44. Interchangeable cartridges 70 of variable source train lengths allow the user to select a cartridge having a source train 43 of the appropriate length to treat the patient. Each cartridge 70 has the capability to store the maximum length source train 43, which may be up to 60 mm for coronary vessels and up to 150 mm for peripheral vessels. A source train 43 that is shorter than the maximum length is accompanied by a retainer (not shown) that maintains the source train 43 immediately adjacent to the pin gate 44 in the distal end of the quartz lumen 72. When inserted into the transfer device, the source cartridge 70 completes the fluid path by fluidly connecting the solenoid valve 68 to channels within the transfer device 10 and the delivery catheter.

With reference to FIG. 4B, the top central portion of the source cartridge has an elongated opening 74 that permits the user to view the transparent quartz sleeve 42. A clear window piece 40 fits within the opening 74 for visual detection of the treatment elements and the pin gate 44, which are housed by the quartz sleeve 42. For magnification of the treatment elements and marker seeds, a magnifying lens could replace the entire window 40. The distal end of the window 40 or magnifying lens may be coupled to a circular lens 76 that further magnifies at least the pin gate 44 and the distal marker seed area of the source train 43.

Figure 6A:
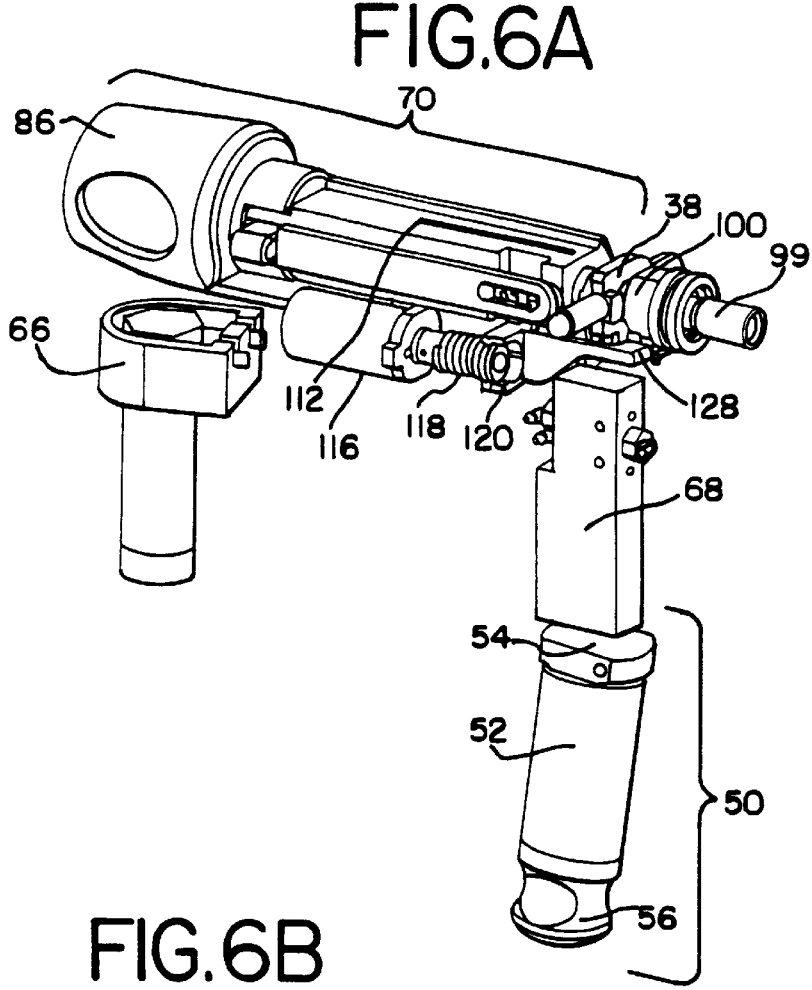
FIGS. 6A and 6B are perspective views of selected internal components of the automated transfer device of FIG. 4.
Figure 6B:
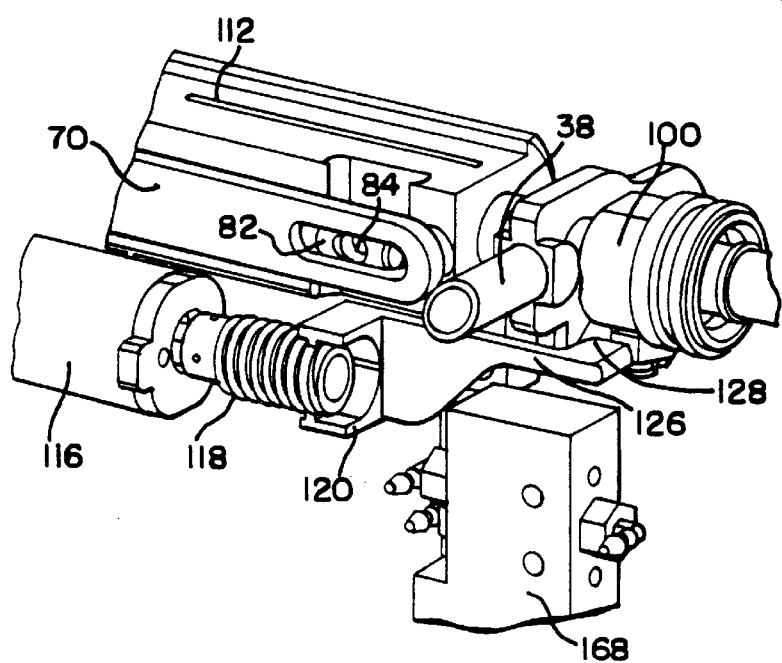

The source cartridge 70 houses the source train 43 in a central lumen 72 that runs along the entire length of the quartz sleeve 42. A pin gate 44, similar to that disclosed within FIGS. 39A and 39B of U.S. Pat. No. 6,013,020, incorporated by reference above, lies within a channel that is perpendicular to the central lumen 72 and that connects the central lumen 72 to the exterior of the quartz sleeve 42. The pin gate 44 is maneuvered between a closed position, where it intersects the quartz lumen 72 to prevent the source train 43 from exiting the quartz 42, and an open position, where it retracts to allow the delivery of the source train 43 into the catheter. Within an opening in the source cartridge 70 and external to the quartz sleeve 42 rest the remaining components of the pin gate mechanism 44: a pin 80, a seal (not shown), a cylindrical bar 82, and a compression spring (also not shown). One end of the spring is affixed to an exposed portion along the source cartridge 70. With reference to FIGS. 6A and 6B, the cylindrical bar 82 has two centrally located circular recessed areas 84, each on opposing sides. The free end of the spring fits within one recess 84 and the head of the pin gate 44 fits within the other recess 84. The seal resides within the quartz channel and closes around the pin gate 44 to create a fluid tight seal as the pin gate 44 is maneuvered back and forth between closed and open positions.

The source cartridge assembly 70 also includes a large knob-like handle 86 for facilitating easy insertion into and removal from the transfer device 10 (best seen in FIGS. 4–6B). The handle 86 may include an indication of the source train length and/or may be color coded to differentiate it from other cartridges 70 that contain different length source trains. The interior of the handle 86 is hollow and houses a spring loaded button 88 with a pin (not shown). The cylindrical portion 90 of the button 88 extends through an opening 92 in the top of the handle 86 and the pin extends through an opening 94 in the side of the handle 86. As the cartridge 70 is inserted into the transfer device 10, the pin (and thus, the button) is forced downward by a negatively sloped overhang 96 on the upper housing portion 18 of the transfer device. Because the pin is an integral with the button 88, the button 88 is forced downward compressing the spring. Once the cartridge 70 is fully engaged, the pin is no longer hindered by the overhang 96, and the bias of the spring forces the pin upward into a notch (not shown). The spring decompresses and the button 88 fully extends. The cartridge 70 can only be removed from the transfer device 10 by depressing the button 88, thereby lowering the pin below the notch. Otherwise, movement of the pin is restricted by the wall of the notch.

Figure 8:
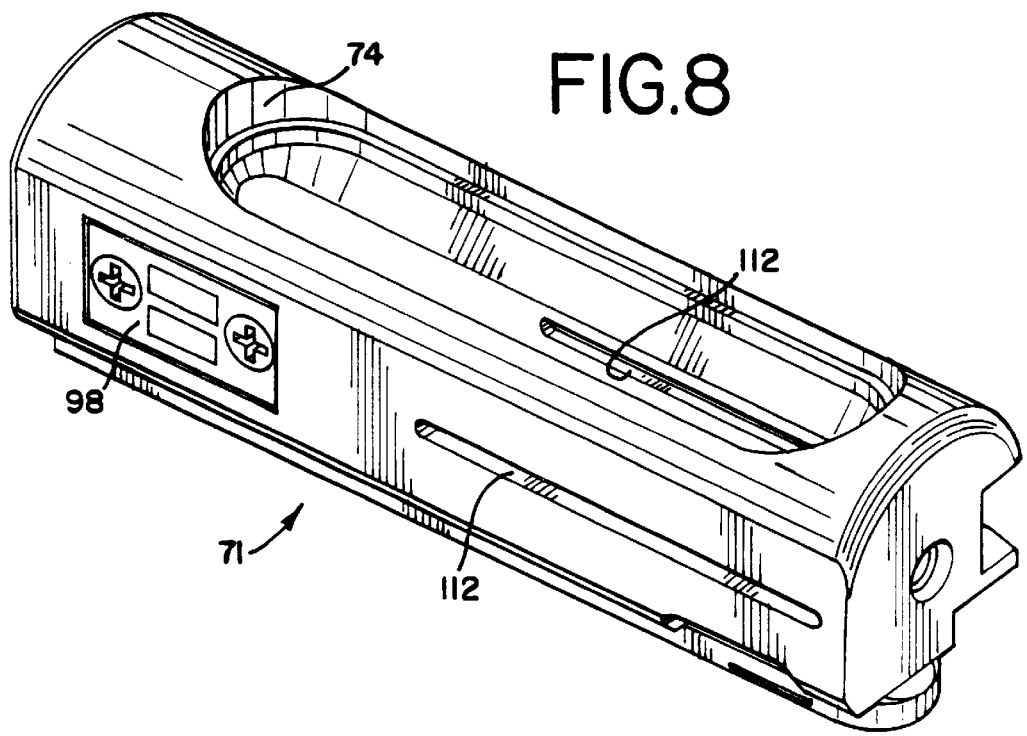
FIG. 8 is a perspective view of an alternative source cartridge to that shown in FIG. 4B.

The source cartridge may also include non-volatile memory that stores specific information regarding the source train 43, such as the its length, its radiation activity, and the number of times it has been used for radiation treatment. The stored data is a compilation of alpha-numeric characters. With reference to FIG. 8, this "smart" cartridge 71 communicates with the transfer device 10 through electronic connectors 98, one within each of the cartridge 71 and the transfer device 10. When the source cartridge 71 is inserted into the transfer device 10, the two electrical connectors come into contact, and the transfer device 10 reads the data stored in the memory and displays it to the user. Based on the information displayed, the user can determine if the desired cartridge 71 has been inserted. The transfer device 10 may also perform a check on the data to make sure it falls within the designated limits. If the data falls outside the limits, the transfer device 10 will indicate an error and will not allow treatment to begin.

The delivery catheter is connected to the transfer device 10 through a proprietary connector 99 located along the catheter's proximal end. The opening in the transfer device 10 for the insertion of the connector 99 is lined with a fluid seal 100 that includes a fluid port 102 in fluid communication with the solenoid valve 68. With reference to FIGS. 5 and 6A, as the connector 99 is inserted into the transfer device 10, it passes through the fluid seal 100, through the connector latch 38, and finally mates with the solid cone member 104 (best seen in FIG. 9) on the distal end of the source cartridge 70. The spring loaded latch 38 must be pressed down for the receipt of the connector 99. Otherwise, the correct sized opening is not aligned with the connector 99. After the connector 99 is inserted, the latch 38 can be released. It springs upward, engaging the undercut portion of the connector 99. The latch 38 must be held down to release the connector 99 from the transfer device 10.

Figure 9:
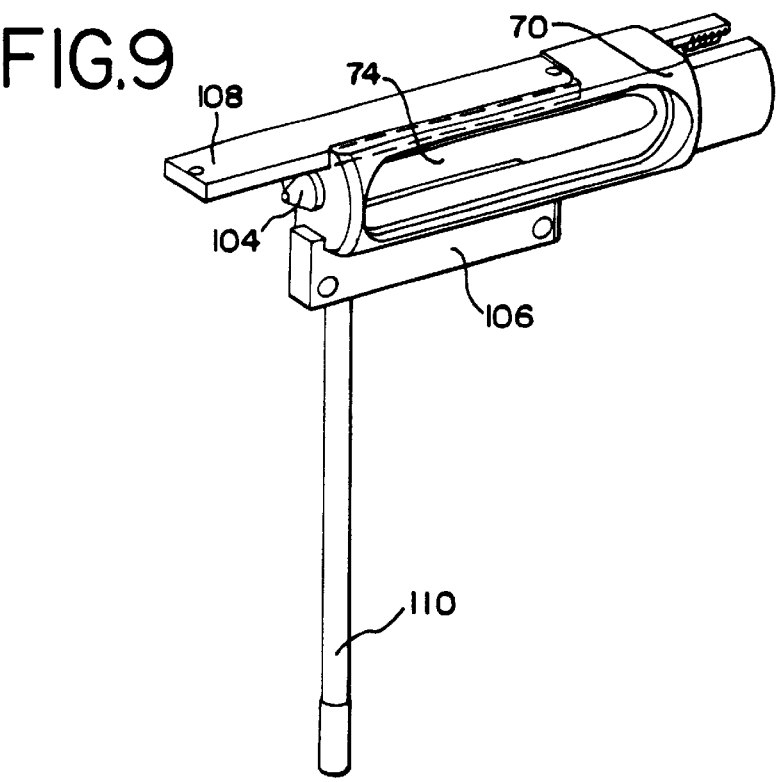
FIG. 9 is a further perspective view of selected internal components of the automated transfer device of FIG. 4.

Prior to disconnecting the catheter or source cartridge 70, the user must be assured that all treating elements are positioned within the quartz housing 42 and behind the closed pin gate 44. Accordingly, in addition to the visual detection of the source train 43, an electronic detection system is included within the transfer device 10. Turning to FIG. 9, the electronic detection system utilizes the combination of a light source 106 (which may be either visible, such as a laser, or infrared light) and a linear CCD (Charged Coupled Device) array 108. The light source 106 and the linear CCD array 108 are positioned on opposite sides of the cartridge 70. The light from the light source 106 travels through a jacketed fiber optic bundle 110 to produce a linear beam or plane of light. The linear beam of light shines through a longitudinal slot 112 along the side of the cartridge 70 and illuminates the pin gate 44 and a portion of the quartz lumen 72. The source cartridge 70 has slots 112 adjacent to both the illuminator 106 and the CCD array 108 to allow the light to pass therethrough (See FIGS. 4, 6B, 8).

The linear CCD array 108 comprises a row of photosensors that measure light directed toward them. If the entire source train 43 is within the housing 18, 20, then the light cast upon the photosensors will be less than when one or more elements is missing. Thus, the electronic system can determine whether or not all treating elements and marker seeds are present by reading the output voltage, which is directly proportional to the amount of light detected by the CCD array 108.

Because of the capability to use variable source train lengths, the optical sensing system detects the presence of only a distal portion of any source train 43. Preferably, at least the distal most five elements of any train 43 will be detected in a given location for a predetermined amount of time. If the last five elements (distal marker seed and four treating elements) of any given source train 43 are present, the user can reasonably assume that the remaining source train elements proximal to the range detected are also be present.

Three indicator LED's 32, 34, 36 (FIG. 1) are visible to user along the face of the transfer device 10. When the electronic detection system senses that the source train 43 is present and the gate 44 is closed, an assigned LED 32 (preferably a green LED) lights up to signal this to the user. When the electronic detection system senses that the source train 43 is missing and/or the gate 44 is open, the green LED 32 turns off and an assigned LED 34 (preferably an amber one) lights up to warn the user. Either the green or amber LED will be lit; it will never be both. The third LED 36 (preferably red), when lit, indicates a low battery. The low battery LED 36 can be lit up simultaneously with either of the other two indicator LEDs 32, 34.

In addition to the electronic detection system for sensing the presence of the source train, other sensors may be included within the transfer device 10 to detect the presence of the fluid cartridge 50, source cartridge 70, and proprietary connector 99. Such sensors may be any of a number of well-known types, such as mechanical, electromechanical (e.g., a leaf spring with a microprocessor measuring its movement or detecting its position), electrical (e.g., a trip switch or limit switch), magnetic (e.g., a reed switch with a permanent magnet), electromagnetic (e.g., Hall effect sensors), or optical sensors. Other types of sensors include displacement and position sensors, proximity sensors, occupancy motion detectors, pressure sensors, and force or strain sensors.

In the illustrated embodiment, for each of the three connections, an optical sensor can be coupled with an illumination source, such as an infrared LED. The illumination sources would be positioned such that each of the fluid cartridge 50, source cartridge 70, and proprietary connector 99 break the light beam of its illumination source when fully inserted into the transfer device 10. The sensor detects the change in the amount of projected light and communicates this with the electronic controls of the system. If one or more of the fluid cartridge 50, source cartridge 70, and delivery catheter are not properly inserted within the transfer device 10, the graphic user interface displays the missing connection(s) and will not allow the user to proceed further until corrected.

The gate actuator assembly 114, best seen in FIGS. 4C and 6, controls the opening and closing of the pin gate 44. It comprises a drive motor 116, a worm gear 118, an attachment or mounting member 120 secured to the worm gear 118 that moves linearly upon rotation of the worm gear, and a U-shaped plate 122. The mounting member 120 has a central portion with a diagonal slot 124 therethrough, a neck 126 extending distally from the central portion with a raised post 128 at its distal-most end, and a long rod 130 extending proximally from the central portion. The U-shaped plate 122 (see FIG. 5) is movably coupled to the slot 124.

In operation, when the user activates the send mode, the motor 116 rotates the worm gear and the attachment 120 moves linearly towards the proximal end of the source cartridge 70. Thus, the mounting member 120 forces the U-shaped plate 122 in a forward position, perpendicular to that of the worm gear 118. The U-shaped plate 122 straddles the pin gate 44 as it intersects the top of the cylindrical bar 82, forcing the pin 80 down into an open gate position.

The gate actuator assembly 114 simultaneously provides additional protection against removing the catheter and/or the source cartridge 70 while the gate 44 is open. The rod 130 moves under the pin extending from the side of the source cartridge handle 86 so that the spring loaded button 88 cannot be pressed downward to disengage the cartridge 70 from the transfer device 10. The raised portion 128 at the distal end of the mounting member 120 moves directly under the shoulder 39 of the latch 38 so that the latch 38 cannot be pressed downward to disengage the proprietary connector 99.

Figure 10:
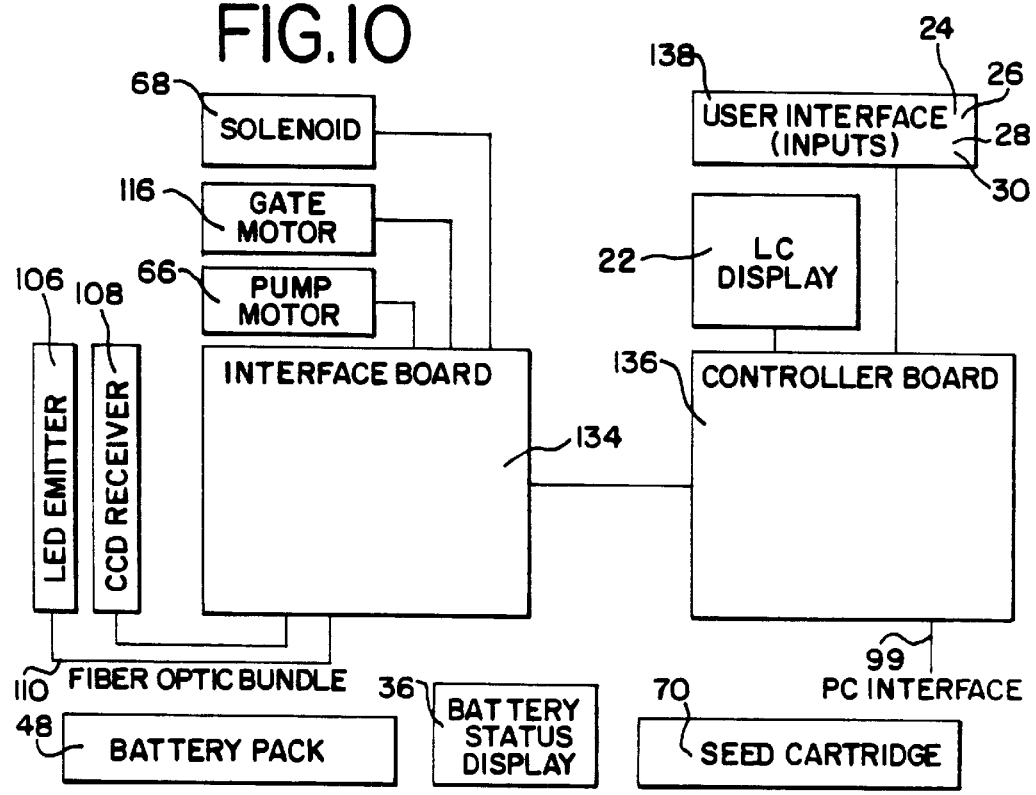
FIG. 10 is a schematic diagram of the system electronics for the automated transfer device of FIG. 1.
Figure 11:
FIGS. 11–22 are graphical representations of a series of display screens that are displayed by the automated transfer device of FIG. 1.
Figure 12:
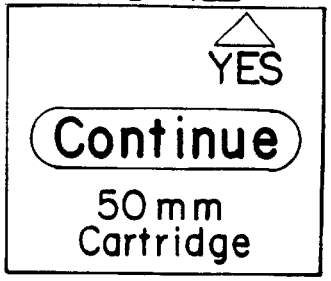
Figure 13:
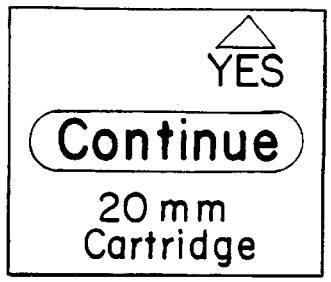
Figure 14:
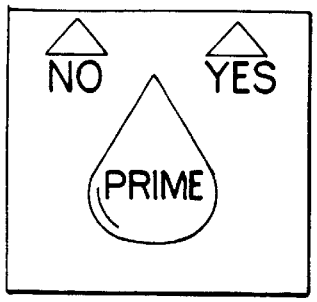
Figure 15:
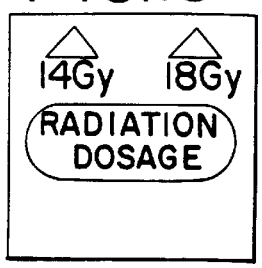
Figure 16:
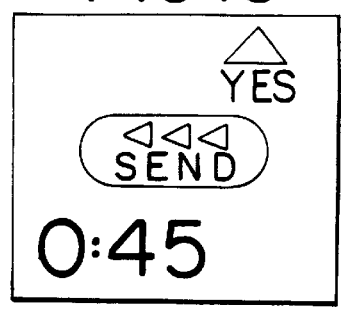
Figure 17:
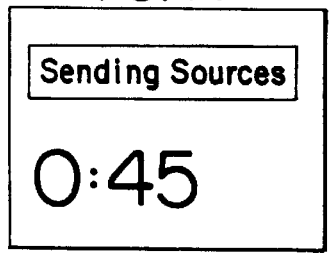
Figure 18:
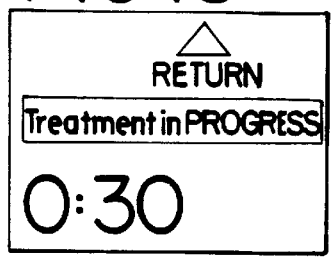
Figure 19:
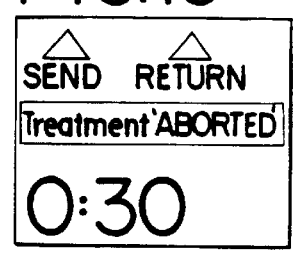
Figure 20:
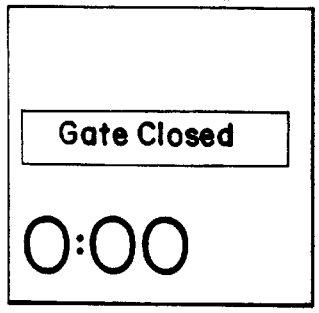
Figure 21:
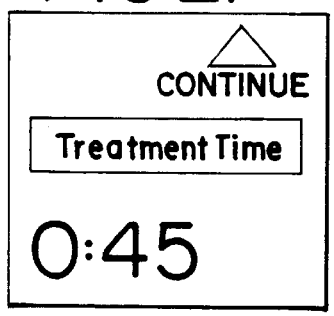
Figure 22:
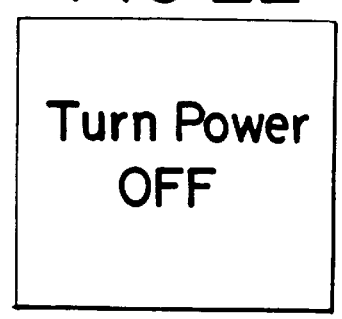

A block diagram of the system electronics is shown in FIG. 10. The electronics are built onto two printed circuit boards, an interface board 134 and a controller board 136. In addition to performing the source sensing algorithms, the interface board 134 drives the pump motor 66, the gate assembly motor 116, the solenoid 68, and the indicator LEDs 32, 34, 36. The controller board 136 displays a series of screens on a LCD 22 (see FIGS. 1 and 5) and commands the interface board 134 based on user inputs 138, which are entered through user interface buttons 24, 26, 28, and 30. The display screens can be designed many different ways depending on how much information the user desires to receive and the level of input to be given by the user.

FIGS. 11–22 show an example of a series of display screens that are useful in assisting the user to perform a radiation treatment procedure. In this example and as shown in FIGS. 1 and 5, the transfer device 10 has three specific function buttons 26, 28, 30 and at least two generic function buttons 24. The specific function buttons are the "POWER" button 26, the "ABORT" button 28, and the "HOME" button 30. However, these buttons 26, 28, and 30 are provided to bypass software interrupters and could be programmed for different functions as needed. The generic function buttons 24 correspond to display prompts and are backlit when associated with an input of an individual screen. If an individual display screen does not have an input associated with a generic button 24, then that button will be disabled. An LED is placed underneath each button 24, 26, 28, and 30; however, only the active buttons for each individual screen will be backlit.

Pressing the "POWER" button 26 turns on the electronics. As the system powers up, the electroluminescent or LED backlighting illuminates, and all LEDs flash on and off for a period of time to indicate that the system is operative. The green LED 32 remains lighted if the source sensing system determines that the pin gate 44 is closed and the treatment elements are stored within the quartz housing 42. Otherwise, the amber LED 34 is lighted to indicate missing treatment elements or an open pin gate 44.

The first display screen (FIG. 11) identifies the manufacture of the device for a short amount of time, and then the system automatically flashes the second screen, which prompts the user to choose between two or more source trains. Upon the user choosing one, the system then moves on to a new screen (FIG. 12 or FIG. 13 depending on choice of 50 mm or 20 mm cartridge) that asks for conformation of the user's choice.

The user can stop the procedure at any time by pressing the "ABORT" button 28 on the face of the transfer device 10. To continue, the "yes" button 24 is pressed and the priming screen (FIG. 14) prompts the user to decide if the device 10 shall be primed with fluid prior to the delivery of the treatment elements. If "no" is chosen, the system immediately goes to the radiation dosage screen (FIG. 15), which prompts the user to choose a dose of either 14 Gy or 18 Gy. Otherwise, the pump 66 and the solenoid 68 become active and pump fluid through the device's fluid channels while maintaining the treatment elements within the source cartridge 70.

The next screen (FIG. 16) displays the treatment time based on the prescribed dosage and information stored in the smart cartridge and prompts the user to begin the treatment. When the send mode is initiated, the pump 66, solenoid 68, and gate actuator assembly 114 work together to send the treatment elements to the distal end of the catheter. The amber LED 34 lights up in place of the green LED 32 when the pin gate 44 opens and the source train 43 exits the quartz sleeve 42. At this point, a new screen (FIG. 17) appears stating that it is waiting for the treatment elements to get to the end of the catheter.

Once the treatment elements are in place, the speed of the pump is reduced by 50% for maintaining the treatment elements at the desired location and the following display screen (FIG. 18) begins to countdown the treatment time. As the treatment time approaches zero, the pump 66 resumes full speed for returning the treatment elements. As soon as the treatment time is over, the solenoid valve 68 reverses the direction of the fluid flow, and the treatment elements are forced back into the quartz sleeve 42.

Once the treatment elements have returned, the optical sensing system detects the presence of the source train 43, the gate 44 moves into the closed position, and the pump 66 and solenoid 68 are turned off. The green LED 32 is illuminated in place of the amber LED 34 to indicate the presence of the treatment elements to the user. The next screen (FIG. 20) confirms that the gate 44 is closed. The next to the last screen (FIG. 21) displays the final treatment time (the initial set time minus the return time), and the last screen (FIG. 22) prompts the user to turn off the system power.

If for any reason the user wanted to abort the treatment once in progress, it can be done by pressing the "ABORT" button 28. This will freeze the timer and activate the screen shown in FIG. 19. The user is given the option to immediately return the treatment elements to the transfer device 10 or to continue sending the treatment elements for treatment. If the returning the source train 43 to the transfer device 10 is the choice, screens depicted in FIGS. 20–22 follow as described previously. If the choice is to resume sending the source train 43 for treatment, then screens depicted in FIGS. 18, 19, 20, 21, and 22 follow as described previously.

Also, at any time following the release of the source train 43 into the delivery catheter, the user has the option to automatically return the source train 43 to the transfer device 10 by depressing the "HOME" button 30. An additional series of display screens are shown collectively in FIGS. 25 A–PP, which consists of forty-two individual screens laid out sequentially.

The transfer device 10 can be connected to any of the catheters that are disclosed in the patent and applications previously incorporated herein by reference. Additionally, catheters 140, 142, having the cross-sections illustrated in FIGS. 23–24, may be used to deliver the treatment elements to a selected site within a patient. Catheters 140 and 142 may be constructed of any material, or a combination of materials, such as nylon, PEBAX, polyethylene, and polyurethane. A proximal segment 144 (FIG. 23A) and a distal segment 146 (FIG. 23B), each of different durometer and stiffness characteristics, are co-extruded and fused together, or variably extruded, to create an elongated catheter 140 having four lumens: a source train delivery lumen 148, two fluid return lumens 150, and a guidewire lumen 152. All four lumens extend along the entire length of the catheter 146, and the source train lumen 148 communicates at its distal end with both fluid return lumens 150.

As seen in FIG. 23B, the distal segment 146 of the catheter 140 has a non-circular cross-sectional shape, with a reduced profile along its length to provide pathways 154 for the perfusion of blood. As a result of the reduced profile, the distal segment 146 of the catheter 140 has increased softness and flexibility, which allows for easier and farther advancement of the distal segment, especially into the more distal and tortuous regions within the human body. Additionally, the softer distal segment 146 improves catheter trackability over a guidewire and creates an atraumatic tip for lessening intraluminal damage as the catheter travels through the patient to the lesion site. The proximal segment 144 of the catheter 140 is circular, unlike the distal segment 146, and utilizes its increased mass and stiffness to advance the catheter 140 through the tortuous vasculature.

The catheter 142 (FIG. 24) is of a single extrusion and has the same cross-sectional profile along its entire length. This catheter 142 also has a source train lumen 156, two fluid return lumens 158, and a guidewire lumen 160. The guidewire lumen 160 may have a protective liner 162 of, e.g., polyimide, and may be coated with Teflon (polytetraflourethylene) or other lubricious material for easier manipulation of the catheter 142 over a guidewire.

The treatment elements and marker seeds of source train 43 (see FIG. 4) may also be any of those described in the patent and applications previously incorporated herein by reference. A source train 43 consists of a series of treatment elements and two marker seeds, one at each end of the source train 43. Preferably, the treatment elements are radioactive cylinders. The marker seeds are used to properly position the treatment elements at the treatment site and are preferably gold or gold plated, since gold is visible under fluoroscopy, which is used to monitor the radiation therapy.

Accordingly, an intraluminal radiation treatment system has been disclosed that meets all the objects of the invention. While the system has been described in terms of a preferred embodiment, there is no intent to limit the invention to the same. Instead, the invention is defined by the following claims.

What is claimed:

1. A transfer device comprising a lumen usable in a system for intraluminal treatment of a selected site in a body of a patient by at least one discrete treating element adapted to be advanced through the lumen in the transfer device into a lumen of a separate catheter by means of pressurized fluid, the transfer device and the catheter defining a closed fluid path for pressurized fluid, the transfer device further comprising an integral pump for pressurizing and circulating the fluid through the fluid path and a removable fluid cartridge including a reservoir from which fluid is drawn by the pump and to which fluid is returned after being circulated through the closed fluid path.

2. The transfer device of claim 1 wherein the integral pump comprises a peristaltic pump.

3. The transfer device of claim 1 wherein the integral pump comprises a reversible peristaltic pump.

4. The transfer device of claim 1 wherein the fluid cartridge includes an elongated fluid pick-up having an inlet through which fluid is introduced into the transfer device and sized in length so that the inlet is always submerged in fluid regardless of the orientation of the transfer device.

5. The transfer device of claim 1 further comprising a removable cartridge including a storage sleeve for housing the treating element, the sleeve having a lumen forming part of the fluid path.

6. The transfer device of claim 5 wherein the storage sleeve comprises a radiation-blocking material.

7. The transfer device of claim 6 wherein the radiation blocking material comprises quartz.

8. The transfer device of claim 5 wherein the removable cartridge further comprises a memory for storing and indicating selected information about the treating element.

9. The transfer device of claim 1 further comprising an external access point to the fluid path adapted to receive an external source of pressurized fluid.

\* \* \* \* \*